(12) United States Patent
Ratterree et al.

(10) Patent No.: US 9,119,927 B1
(45) Date of Patent: Sep. 1, 2015

(54) APPARATUS AND METHOD FOR INTUBATING HUMANS AND NON-HUMAN ANIMALS

(76) Inventors: Jerry Blaine Ratterree, Murietta, CA (US); Robert G. Seebold, Canyon Lake, CA (US); Robert D. King, Rochester, MN (US)

( * ) Notice: Subject to any disclaimer, the term of this patent is extended or adjusted under 35 U.S.C. 154(b) by 445 days.

(21) Appl. No.: 12/783,545

(22) Filed: May 19, 2010

Related U.S. Application Data

(60) Provisional application No. 61/179,692, filed on May 19, 2009.

(51) Int. Cl.
*A61M 16/00* (2006.01)
*A61M 16/04* (2006.01)

(52) U.S. Cl.
CPC ....... *A61M 16/0447* (2014.02); *A61M 16/0445* (2014.02); *A61M 16/0434* (2013.01); *A61M 16/0465* (2013.01)

(58) Field of Classification Search
CPC ..................... A61M 16/04; A61M 2016/0409; A61M 16/0434; A61M 16/044; A61M 16/0465; A61M 1/008; A61M 16/0443; A61M 16/0445; A61M 16/0447; A61M 25/0041; A61M 27/006; A61M 2210/065; A61M 2210/0656; A61M 16/049
USPC ............ 128/200.24, 200.26, 204.18, 207.14, 128/207.15, 207.18; 604/96.01, 98.01
See application file for complete search history.

(56) References Cited

U.S. PATENT DOCUMENTS

| | | | |
|---|---|---|---|
| 3,516,410 A | 6/1970 | Carrera | |
| 3,599,642 A | 8/1971 | Tindel | |
| 3,616,799 A | 11/1971 | Sparks | |
| 3,659,611 A | 5/1972 | Miller | |
| 3,810,474 A * | 5/1974 | Cross | 128/207.15 |
| 4,502,482 A | 3/1985 | De Luccia et al. | |
| 5,251,617 A | 10/1993 | Linder | |
| 5,285,777 A | 2/1994 | Beckwith | |
| 5,305,740 A | 4/1994 | Kolobow | |
| 5,322,062 A * | 6/1994 | Servas | 128/207.14 |
| 5,429,127 A | 7/1995 | Kolobow | |
| 2003/0192552 A1* | 10/2003 | Mongeon | 128/207.14 |
| 2008/0000482 A1* | 1/2008 | Maguire et al. | 128/207.15 |
| 2010/0154797 A1* | 6/2010 | Landis et al. | 128/205.27 |

* cited by examiner

*Primary Examiner* — Tan-Uyen (Jackie) T Ho
*Assistant Examiner* — Mark K Han
(74) *Attorney, Agent, or Firm* — Charles A. Lemaire; Lemaire Patent Law Firm, P.L.L.C.

(57) ABSTRACT

The present invention provides an apparatus and a corresponding method for intubating a human or non-human animal patient. In some embodiments, the present invention is used in the field of anesthesia and emergency medicine. In some embodiments, the present invention provides an intubation tube that includes an integrated Blaine Bafflex System having a plurality of blaines for sealing the trachea, wherein the intubation tube is formed from a single material. In some embodiments, the shape and outer circumference of each blaine of the system is selected according to the desired use of the intubation tube (e.g., for intubating a pediatric patient or an adult patient or for intubating a small animal or a large animal). In some embodiments, the distance between successive blaines is selected such that, when the intubation tube is inserted into the patient and the blaines bend, none of the blaines overlap with their nearest neighbor.

21 Claims, 8 Drawing Sheets

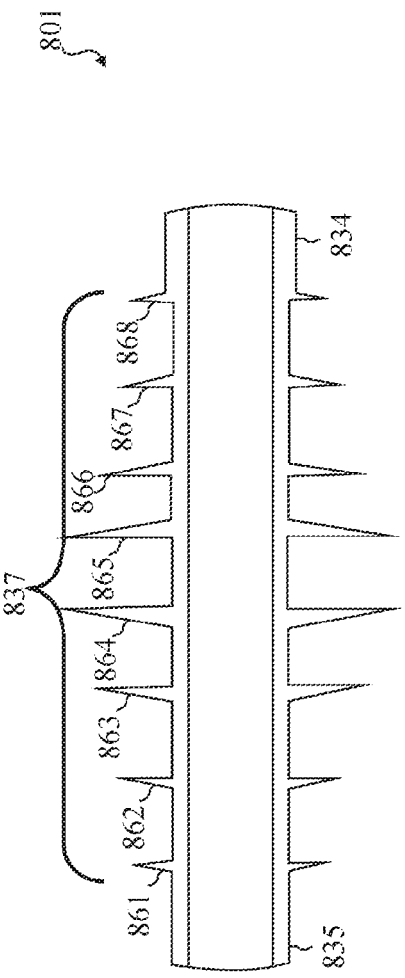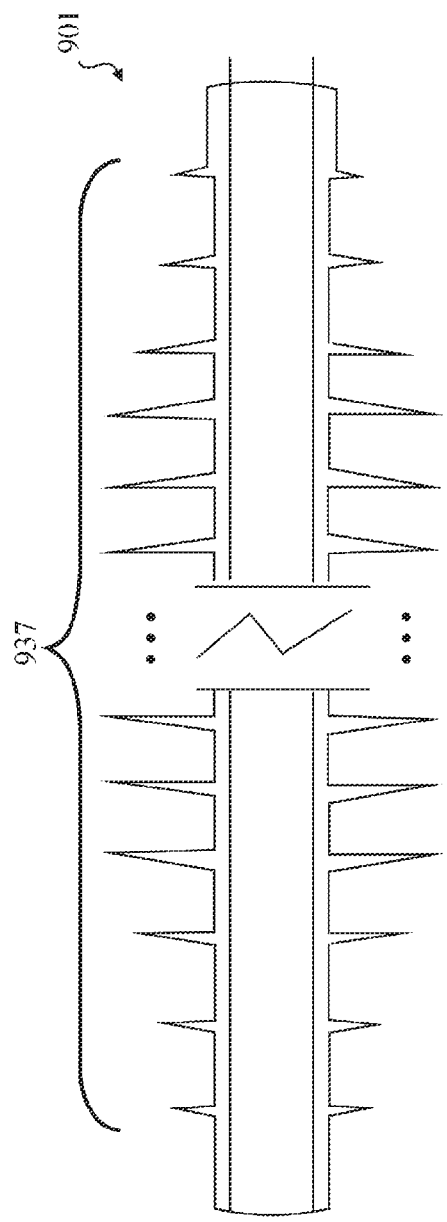

APPARATUS AND METHOD FOR INTUBATING HUMANS AND NON-HUMAN ANIMALS

RELATED APPLICATIONS

This Application claims benefit under 35 U.S.C. §119(e) of U.S. Provisional Patent Application 61/179,692 filed on May 19, 2009, titled "Omnivet Safe-Seal Endotracheal Tube," which is incorporated herein by reference in its entirety.

FIELD OF THE INVENTION

The present invention relates to the field of medical devices and methods, and more specifically to medical devices for patient intubation and surgical methods for intubating a patient in preparation for a surgical procedure(s).

BACKGROUND OF THE INVENTION

Intubation tubes (e.g., endotracheal, nasotracheal, and tracheostomy tubes; also called lumens) are used during medical procedures during the administration of anesthesia and critical care medicine and are used to provide access to the upper airways for controlled, assisted ventilation or spontaneous unassisted ventilation.

Conventional intubation tubes available in the market have many inherent dangers related to their complicated design and friability. Further, conventional endotracheal tubes have problems with leakage, due to both over pressurization of the trachea and under pressurization of the trachea, which allows fluids to enter the lungs.

There exists a need for a safer, easier and less invasive method to intubate patients in preparation for a surgical procedure. Intubating patients means to provide a way for the patient to 'breathe' during surgery and the traditional method is placing an endotracheal tube down a patient's throat and connecting the tube to a respirator or anesthetic machine. It is necessary for the traditional procedure to have an inflatable ball, or cuff, to seal the tube inside the patient's throat. The tubes currently available are basically made to be disposable and because of their complicated design and moving parts and poor construction, they are very friable and have to be replaced constantly due to failure of the inflation system. Failure of the inflation system during anesthesia can and has been fatal to many patients. The traditional method must be performed by a trained professional because if intubation is performed incorrectly there are risks of damaging the lining of the trachea or even causing tracheal rupture which can lead to death of the patient. It is worth noting that for both human use and animal use (i.e., veterinary use), technicians receive specific training and are certified for the traditional intubation procedure.

Another complication caused by conventional intubation tubes is that it is necessary to maintain several different sizes of traditional tubes to avoid damaging the patient's trachea or larynx by selecting the wrong size. This is especially evident in veterinary use where as many as 14 sizes or more are required to intubate the various sizes of dogs, cats and farm animals. Selecting the correct traditional tube size is very important and underscores the need for a trained technician to implement the traditional method of intubation. The number of sizes creates inventory issues and leads to confusion as to the storage of the traditional tubes.

Conventional intubation tubes and technology use inflation cuffs that allow many dangers to the patient. If the cuff fails or leaks during surgery, which they often do, the patient can wake up during surgery because of not receiving the necessary anesthetic or oxygen, and can also aspirate fluids. More dangerously, the cuff can be over inflated quite easily and cause damage and pressure necrosis to the tracheal mucosa or even tracheal tearing or rupture. The current method used to evaluate the pressure in the inflated cuff is a palpation bulb on the outside of the tube which the operator is supposed to feel and judge the pressure in the cuff. This is at best a crude measurement of the true pressure inside the trachea, and studies have shown that, at times in certain studies, over 50% of the time, the cuff is over inflated causing damage to the trachea. This has become such a wide spread issue that there are now commercial devices such as the Olympic Cuff-Safe™ that is a handheld device that more accurately measures the cuff pressure of the cuffs.

U.S. Pat. No. 3,659,611 filed Dec. 15, 1969, titled "Tracheal Tube Seal" by Don R. Miller, which is incorporated herein by reference in its entirety, describes an improvement in tracheostomy and endotracheal tubes for effecting a substantial air seal between the tube and the trachea and further provides on the periphery of the indwelling portion of the device a series of thin resilient, circular flanges, of silicone rubber, wherein the flanges bend for insertion and withdrawal and engage the wall of the trachea to form an air seal therewith.

U.S. Pat. No. 5,429,127 filed Jul. 6, 1993, titled "Thin Wall Endotracheal Tube" by Theodor Kolobow, which is incorporated herein by reference in its entirety, describes an ultra-thin wire reinforced endotracheal tube which includes a novel sealing design adapted to fit in a complementary manner in a subject's larynx and the endotracheal tube includes a laryngeal section which has a cross sectional shape and size that are complementary to a subject's glottis and preferably, the laryngeal section has an oval or egg-shaped cross section and a plurality of thin, pliable sealing "gills" are provided on the surface of the laryngeal section, wherein the gills provide a fluid tight seal which does not harm a subject's larynx and the endotracheal tube is reinforced with a metallic spring material and in a preferred embodiment, the metallic spring material is a shape memory alloy and the use of a shape memory alloy prevents damage to the endotracheal tube caused by distortion, such as kinking, crushing, etc.

U.S. Pat. No. 5,305,740 filed May 6, 1992, titled "Sealing Means For Endotracheal Tubes" by Theodor Kolobow, which is incorporated herein by reference in its entirety, describes a sealing element for a tubular member such as an endotracheal tube which includes a circular collar portion and a pliable flange or gill, wherein one or more of the sealing elements are positioned on a tubular member such as an endotracheal tube and when the tubular member is inserted into a lumen such as a trachea, the pliable flange(s) or gill(s) forms a seal between the outer wall of the tubular member and the inner wall of the lumen and, in the case of endotracheal tubes and the sealing elements replace conventional inflatable cuffs and allow for tubes having diameters less than 5 mm.

U.S. Pat. No. 5,285,777 filed Aug. 8, 1991, titled "Tracheostomy Apparatus" by Wayne E. Beckwith, which is incorporated herein by reference in its entirety, describes a flexible support plate member mounts straps at opposed ends thereof for securement about an individual, with the plate member receiving a tracheal tube through a receiving plate bore in pivotal relationship, with the tracheal tube including an expandable balloon seal positioned adjacent a lower terminal end of the tracheal tube, with a suction conduit arranged for reception of a catheter tube and a modification of the invention includes sealing ribs and adhesive mounted about the balloon to enhance sealing within the individual.

U.S. Pat. No. 3,516,410 filed Jan. 3, 1968, titled "Cerebro-Ventricular Catheter" by Salomon Hakim, which is incorporated herein by reference in its entirety, describes a ventricular catheter for use with ventriculoatrial shunting devices, and consists of a tubing of soft, tissue-compatible material with intake apertures positioned in the wall of the tubing at one end thereof, the end of the tubing preferably being closed and thin membranes of flexible, tissue-compatible material are attached between the holes and extend outward from the wall of the tube wherein the flexibility is such that the lightest contact with attached tissue will bend the membrane and protect the underlying hole and the membrane may be radially slit to facilitate collapsing upon passing of the catheter through tissue and the membranes are long enough, so that when the catheter is inserted in tissue, they cover the apertures to prevent scraping of tissue thereby.

U.S. Pat. No. 5,251,617 filed Dec. 11, 1992, titled "Endotracheal Tube With Concentrically Mounted And Axially Slidable Connector" by Gerald S. Linder, which is incorporated herein by reference in its entirety, describes a flexible, cylindrical endotracheal tube is disclosed employing an axially slidable, hollow, cylindrical connector concentrically mounted upon the outer surface of the endotracheal tube near its proximal end; the proximal tip of the endotracheal tube is provided with an annular flange having an outer diameter larger than the inner diameter of the hollow output section of the slidable connector and smaller than the inner diameter of the hollow input section of the connector; a breathing circuit connector may be attached to the hollow input section of the slidable connector for coupling to the hoses of a conventional anesthesiology machine; the slidable connector is axially positionable over the outer surface of the proximal end portion of the endotracheal tube without loss of the airtight seal; the annular, flanged tip of the endotracheal tube may pass into and through the bore of the breathing circuit connector during positioning of the slidable connector; the axial positioning of the slidable connector may occur before intubation, after intubation, or while the patient is in recovery.

U.S. Pat. No. 4,502,482 filed Aug. 11, 1983, titled "Endotracheal Tube Complex" by Victor C. DeLuccia, et al., which is incorporated herein by reference in its entirety, describes an endotracheal complex for insertion into the trachea of a patient, and wherein the trachea branches through the carina trachea distally into two bronchi, includes a tube which has a distal blunt and atraumatically shaped tip so as to restrain passage of the tip beyond the carina tracheae into the bronchi and to serve as an internal palpator to identify an anatomical reference point, and an inflatable cuff near the tip for preventing any air or air component other than oxygen emanating from the source of oxygen to pass to the bronchi; a removable introducer is disposed in the tube and has a beveled end portion to facilitate insertion of the tube through the larynx into the trachea; after the endotracheal tube is inserted into the trachea of a patient, the beveled end portion is removed by pulling on the introducer tube or stylet; the beveled end portion collapses off the blunt end of the endotracheal tube and can be pulled through the endotracheal tube to be removed and discarded; the remaining blunt end of the endotracheal tube, from which oxygen is fed to the patient, is so designed so that it will slip past the carina trachea into either bronchus of the patient; there is also provided a suction tube which fits into the endotracheal tube and which has a distinct curve at its distal end as it emerges from the blunt end of the endotracheal tube so that it can be easily directed to slide down the left or right bronchus of the patient in order to aspirate fluids from the lung.

U.S. Pat. No. 3,616,799 filed Oct. 6, 2009, titled "Tubes With Sail Cuffs For Tracheal Intubation" by Charles H. Sparks, which is incorporated herein by reference in its entirety, describes a cuff having an open ended flaring skirt which is pressed against the tracheal wall during the positive pressure phase of mechanical ventilation of the patient's lungs, wherein the sealing pressure is applied by the ventilating gas itself whereby the pressure of the cuff against the tracheal wall can never exceed that of the ventilating gas and whereby the cuff is relaxed in each breathing cycle when the ventilating gas is not above atmospheric pressure and a slidable sleeve sheaths the skirt for intubation and unsheaths the skirt after intubation, wherein the cuff is used on endotracheal, nasotracheal and tracheostomy tubes.

U.S. Pat. No. 3,599,642 filed Dec. 29, 1969, titled "Endotracheal Tubes" by Roland L. Tindel, which is incorporated herein by reference in its entirety, describes disposable endotrached tubes, wherein the tubes have an adapter portion integral with a body portion through a juncture, with a lumen of substantial constant diameter extending throughout the body portion and juncture, the lumen opening into the adapter through a region of generally nonturbulent flow and, wherein the juncture portion is corrugated to provide a flexible connection at any desired angle between adapter and body portion.

What is needed is an improved apparatus and method for intubating patients.

SUMMARY OF THE INVENTION

The present invention provides an apparatus and method for intubating humans and animals using an intubation device having blaines in a bafflex system.

In some embodiments, the present invention provides an apparatus that includes an intubation device having a flexible lumen having a proximal end and a distal end and a plurality of spaced-apart flexible resilient annular blaines located between the distal end the proximal end and formed integral on the lumen as a single piece, wherein the distal end is configured to be inserted into a body passage and the proximal end is configured to be outside the body and attached to a medical device.

In some embodiments, the present invention provides a method that includes providing an intubation device that includes a flexible lumen having a proximal end and a distal end and a plurality of spaced-apart flexible resilient annular blaines located between the distal end the proximal end, and formed integral on the lumen as a single piece; and sterilizing the intubation device as a single piece in its entirety.

In some embodiments, the present invention provides an intubation device that includes a flexible lumen having a distal end for insertion into a body passage, and a proximal end; and a plurality of spaced-apart flexible resilient means (as described and shown herein) for sealing between the lumen and the body passage. In some embodiments of this apparatus, an outer circumference of each one of the plurality of flexible resilient means for sealing are substantially circular. In some embodiments of this apparatus, at least two of the plurality of flexible resilient means for sealing have a first face that is substantially conical and an opposite second face that is substantially planar. In some such embodiments, at least two of the plurality of flexible resilient means for sealing have a first face that is substantially conical facing the distal end of the lumen and an opposite second face that is substantially planar, while at least two others of the plurality of flexible resilient means for sealing have a first face that is substantially conical facing the proximal end of the lumen and an opposite second face that is substantially planar.

BRIEF DESCRIPTION OF THE DRAWINGS

FIG. 8 is a schematic side-view cross-section of an endotracheal tube portion 801, wherein the outer circumference of each of the plurality of blaines is selected to provide a desired function, according to some embodiments of the present invention.

FIG. 9 is a schematic side-view cross-section of an endotracheal tube portion 901 having two sets of blaines, wherein each set includes a plurality of blaines and wherein the two sets of blaines are separated a lateral distance, according to some embodiments of the present invention.

DESCRIPTION OF PREFERRED EMBODIMENTS

Figure 1B:
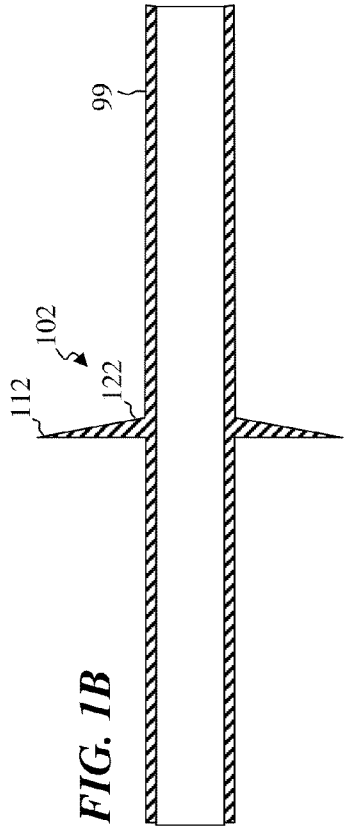
FIG. 1B is a schematic side-view cross-section of a single blaine 102, according to some embodiments of the present invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, the term "blaine" refers to a parasol-shaped flange-type or fin-type extension feature located surrounding and affixed to a tube (in some embodiments, the outer circumference of the blaine is concentric with the axis of the tube, while in other embodiments the axis of the tube is laterally offset relative to the center of the blaine), wherein, in some embodiments, the blaine has a first face that is substantially flat and a second and opposite face that is tapered and thinner at the outer radius and thicker towards the center of the blaine. In some embodiments, the outer circumference of each blaine is substantially circular; in other embodiments the outer circumference is an elliptical or otherwise convex shape.

As used herein, the term "Blaine Bafflex System" refers to a system of one or more blaines integrated with a tube (also called a lumen) for use in patient intubation. In some embodiments, the "Blaine Bafflex System" includes a plurality of blaines wherein the size and shape of each blaine is selected in order to satisfy the requirements for a particular patient or medical procedure.

The present invention is related to surgical devices for intubating human patients and non-human animal patients and for methods for use in the field of anesthesia and emergency medicine. More specifically, the present invention provides a new endotracheal tube that eliminates the risks inherent in conventional endotracheal tubes. In some embodiments, the present invention is used for endotracheal, nasotracheal, and tracheostomy tubes, and the like.

In some embodiments, the present invention provides an endotracheal tube that provides enhanced safety for the patient by eliminating the risk of damage caused by convention tubes using inflation cuffs. The tube of the present invention is easy and safe to use and less training in the use of the tube of the present invention is required and the guesswork involved with present day conventional endotracheal tube technology is significantly eliminated. The tube of the present invention provides durability surpassing conventional tubes as well as economic benefit because the tube of the present invention can be sterilized and reused. Conventional tubes are made disposable by design and therefore not as cost effective as the present invention. Ultimately, the present invention is safer for the patient, eliminates guesswork on the part of the practitioner, provides ease and cost effectiveness in use, is a more durable product, and has significantly reduced the medical risks associated with intubating a patient.

In some embodiments, the present invention provides a method and apparatus that eliminates the current complications of inflation cuff intubation tubes. In some embodiments, the method includes the use of an apparatus that does not have any moving parts, is one solid piece of medical grade silicone and which significantly reduces the change of tube failure or leakage. In some embodiments, the one solid, molded piece mitigates the inherent risks of contaminations and infections by eliminating the need for assembling multiple parts made from different materials and, in addition, the thicker end of the tube helps prevent damage caused from biting on the tube by the patient.

The present invention provides the Blaine Bafflex System that employs a design of about three (3) or more tapered silicone blaines that create a safe seal in the trachea with significantly reducing the danger of leaking or causing undue pressure on the lining of the trachea. Because of the one-piece construction and silicone material, the tube of the present invention is autoclaveable, meaning that it can be sterilized with standard equipment with the option of being re-usable.

In some embodiments, the Blaine Bafflex System design provides a cleansing of the trachea upon removal of the tube by gently wiping the walls of the trachea as the tube is extracted. Conventional tubes with inflation cuffs require deflating the cuff which allows accumulated fluids to pass into the lungs. In some embodiments, the method of use of the Blaine Bafflex System eliminates or reduces the need to raise and tilt the patient to prevent aspiration, thus leaving the patient in a safer and more comfortable position and the inventors believe that no other endotracheal tube available can claim the safety, durability, ease of use, or cost effectiveness of a this Blaine Bafflex System intubation tube.

In some embodiments, the endotracheal tube of the present invention is directed to a novel seal means used in conjunction with ultra thin blaines of varying diameters and shapes. In some embodiments, working in conjunction, the blaines, or specially designed baffles, effectively provide a fluid and air seal between the outer wall of the tube and the lumen into which the tube is to be inserted and therefore eliminates or significantly reduces the dangers associated with patient intubation, is much more user-friendly requiring little training of the operator, and is much more durable, economical and safe.

In some embodiments, the present invention provides an intubation tube having the Blaine Bafflex System that includes a one piece construction, made of 100% silicone, autoclaveable using standard equipment, has a straight tube shape, is flexible, uses a tube tip that does not touch the trachea due to the lack of a rigid tube curve and a tube tip that is angled to allow easier insertion through the glottis, and a distance from the end tip to the blaines that allows the practitioner to view the tip insertion. In some embodiments, the blaines of the Blaine Bafflex System have outer circumferences that are different to permit the use of the tube in patients with different size tracheas because the different sized blaines ensures that that one or more will only bend or flex at the tip which does not cause a fold in the blaine, instead of the blains being equally sized which allows for blaine folding and consequently allows air and fluid leaks. In some embodiments, the blaines 102 (see FIG. 1B) are tapered at an 11-degree angle from a thicker base 122 to a thinner outer circumference 112.

In some embodiments, the first three blaines of the intubation tube have the angled side facing proximally and the last three blaines have the angle facing caudally, which allows the tube to seal when moved in either direction.

In some embodiments, the spacing between the blaines is selected to allow the proper amount of sealing without causing undue pressure on the trachea or folding of the blaines. In some embodiments, the proximal portion of the intubation tube is thicker to protect it from patient biting during an intubation procedure.

In some embodiments, the intubation tube includes a flexible shaft and allows patient rotation such that the tip does not cause damage.

In some embodiments, the intubation tube is combined with a stylet that can be made with different materials, PVC, vinyl coated wire, aluminum, copper, or the like, has a length to match the size of the tube, and that has a finger grip to assist with tube insertion. In some embodiments, the stylet is a semi-rigid stylet, a formed curve stylet, or a formable stylet.

In some embodiments, the Blaine Bafflex System is integrated with a tube and used for a non-medical application, such as anytime a smaller tube needs to be sealed inside a larger tube (e.g., putting a small ¼ inch tube in a garden hose to water plants, or inserting a smaller tube in the larger oil change tube to suck the oil out of a boat engine through the dip stick hole, or the like).

In some embodiments, the angled tip of the intubation tube is used to pry the arytenoids cartilages apart to assist with insertion. In some embodiments, because the tip of the intubation tube is always centered in the trachea as opposed to a pre-curved tube, the operator does not have to worry about the tip of the tube being occluded because it is up against the tracheal wall. Conventional curved tubes require a hole in the side of the tube near the tip called a Murphy Eye to prevent the situation in which the normal opening at the tip is occluded because it is up against the tracheal wall. In some embodiments, the present invention removes the need for a Murphy Eye because the operator does not have to observe the ventilation of the patient after intubation to insure the tip of the tube is not occluded.

In some embodiments, the intubation tube is extubated without the need to form an arc or curving hand motion as is required with conventional tubes because the tube of the present invention is flexible, soft, and straight.

In some embodiments, the intubation tube of the present invention is much less costly to manufacture than convention tubes, has no danger of causing pressure necrosis to the trachea, has no danger of accidental deflation causing the patient to wake up or not receive oxygen or anesthetic, is less traumatic to the tracheal mucosa, cleanses the trachea of saliva, mucus, and other fluids upon extubation, therefore eliminating the risk of aspiration after removal, as opposed to conventional inflation cuff tubes which release any fluids trapped proximal to the inflation cuff when the cuff is deflated.

In some embodiments, the intubation tube of the present invention is much more rapidly installed due to the fact that no inflation is necessary, over inflation of the patient's lungs due to error made by the operator of the anesthetic machine, such as accidental closure of the pop-off valve, is totally prevented because the design of the silicone baffles allows pressure exceeding 20 cm of water to bypass the valve instead of over pressurizing the lungs, higher air flow capacity compared to traditional tubes because smaller tubes are used compared to the standard conventional inflation tubes and attain the same flow of oxygen and anesthetic, have much less maintenance, are easier to clean and sterilize, and need to be replaced much less often, possibly many years.

In some embodiments, the endotracheal tube of the present invention does not depend upon an air inflated cuff but rather uses a series of six blaines with a particular pattern and spacing to seal the trachea without pressure. In some embodiments, the flexible blaines are tapered and spaced allow an "o-ring effect", such that when the patient inspires, the baffles are held tightly against the tracheal wall and on expiration the special design allows passage of air/anesthetic if the pressure exceeds 20 pounds per square inch, thus preventing over-pressurization of the lungs. In some embodiments, the soft, flexible blaines are atraumatic to the tracheal surface and also provide a "squeegee" effect when extubating, by scraping the trachea clean of mucous, saliva, vomitus, blood or any other foreign material and when inserted, the end of the tracheal tube lies in the trachea and the sealing baffles are touching the tracheal wall, leaning rostrally (i.e., the tips of the baffles are facings towards the larynx) such that when the patient inspires, the silicone baffles are held tightly against the trachea. In some embodiments, if positive pressure is desired either by a respirator, or manually, the anesthesiologist merely withdraws the endotracheal tube one-half inch, and the baffles will flip over and the tip will be facing caudally thereby allowing as much pressure to be applied as deemed necessary by the operator.

In some embodiments, the end of the tracheal tube reduces the dangers of deflation or over inflation thus preventing most of the hazards of conventional inflation-cuff technology and, in addition, the present invention provides more rapid insertion, cleansing of the tracheal, improvement of longevity, and is generally much more user friendly.

Figure 1C:
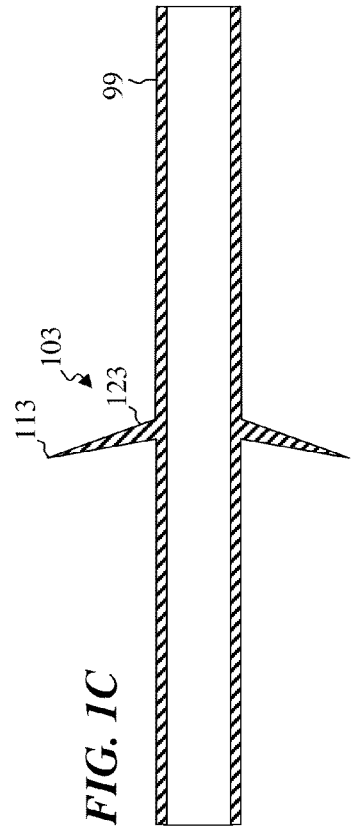
FIG. 1C is a schematic side-view cross-section of a single blaine 103, according to some embodiments of the present invention.
Figure 1D:
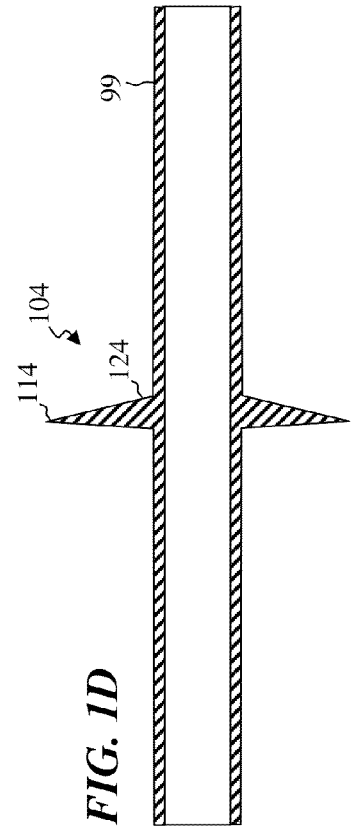
FIG. 1D is a schematic side-view cross-section of a single blaine 104, according to some embodiments of the present invention.
Figure 1A:
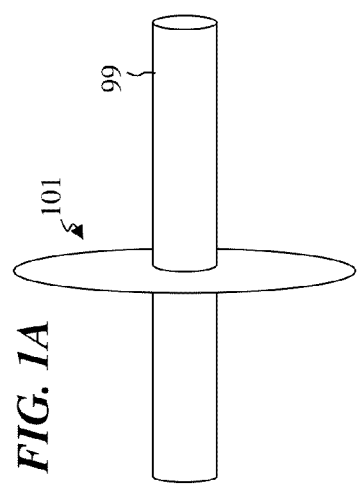
FIG. 1A is a schematic perspective view of a single blaine 101, according to some embodiments of the present invention.

FIG. 1A is a schematic perspective view of a single blaine 101, according to some embodiments of the present invention. In some embodiments, the single blaine 101 is a feature that is integrated with and extending from tube 99 and together the blaine 101 and the tube 99 form an intubation tube that is used for intubating human patients and non-human animal patients. In some embodiments, the shape of blaine 101 and the material used to form blaine 101 is selected according to the desired use of blaine 101 (e.g., in some embodiments, the desired use is determined by the size of the patient, the species of the patient, the robustness required for the intubation tube, and the like).

FIG. 1B is a schematic side-view cross-section of a single blaine 102, according to some embodiments of the present invention. In some embodiments, single blaine 102 has a shape that is tapered from blaine base 122 towards blaine edge 112 and is substantially flat on one side of blaine 102 and an opposite side that is angled, with respect to a plane that is perpendicular to the axis of tube 99. In some embodiments, the blaine edge 112 of blaine 102 has a profile that is substantially pointed and in some other embodiments, the outer edge 112 has an edge profile that is rounded, flat, angled, or includes a feature that assists with patient intubation (e.g., in some embodiments, the edge profile is scalloped, concave, ribbed, or the like). In some embodiments, all blaines described herein have an edge profile that is selected based on the specific requirements of the intubation tube and procedure and include at least the edge profiles discussed above. In some embodiments, blaine 102 is thickest 122 where blaine 102 meets tube 99. In some embodiments, the angle of the taper with respect to a plane that is perpendicular to the axis of tube 99 is between about zero degrees and about 1 degree, or between about 1 degree and about 2 degrees, or between about 2 degrees and about 5 degrees, or between about 5 degrees and about 10 degrees, or between about 10 degrees and about 15 degrees, or between about 15 degrees and about 20 degrees, or between about 20 degrees and about 25 degrees, or between about 25 degrees and about 30 degrees.

FIG. 1C is a schematic side-view cross-section of a single blaine 103, according to some embodiments of the present invention. In some embodiments, single blaine 103 has a shape that is tapered from blaine edge 113 towards blaine base 123 and each side of blaine 103 is angled with respect to a plane that is perpendicular to the axis of tube 99. In some embodiments, the first angle with respect to a plane that is perpendicular to the axis of tube 99 of the first side and the second angle with respect to a plane that is perpendicular to the axis of tube 99 of the second and opposite side are both positive and the first angle is greater than the second angle. In some embodiments, the first angle is greater than zero degrees and up to about 1 degree, or between about 1 degree and about 2 degrees, or between about 2 degrees and about 5 degrees, or between about 5 degrees and about 10 degrees, or between about 10 degrees and about 15 degrees, or between about 15 degrees and about 20 degrees, or between about 20 degrees and about 25 degrees, or between about 25 degrees and about 30 degrees. In some embodiments, the second angle is greater than the first angle and greater than zero degrees and up to about and about 1 degree, or between about 1 degree and about 2 degrees, or between about 2 degrees and about 5 degrees, or between about 5 degrees and about 10 degrees, or between about 10 degrees and about 15 degrees, or between about 15 degrees and about 20 degrees, or between about 20 degrees and about 25 degrees, or between about 25 degrees and about 30 degrees.

FIG. 1D is a schematic side-view cross-section of a single blaine 104, according to some embodiments of the present invention. In some embodiments, single blaine 104 has a shape that is tapered from blaine edge 114 towards blaine base 124 and each side of blaine 104 is angled with respect to a plane that is perpendicular to the axis of tube 99. In some embodiments, the first angle with respect to a plane that is perpendicular to the axis of tube 99 of the first side is a positive angle and the second angle with respect to a plane that is perpendicular to the axis of tube 99 of the second and opposite side is negative (or opposite in direction to the first angle). In some embodiments, the first angle is between about zero degrees and about 1 degree, or between about 1 degree and about 2 degrees, or between about 2 degrees and about 5 degrees, or between about 5 degrees and about 10 degrees, or between about 10 degrees and about 15 degrees, or between about 15 degrees and about 20 degrees, or between about 20 degrees and about 25 degrees, or between about 25 degrees and about 30 degrees. In some embodiments, the second angle is between about zero degrees and about minus one (−1) degree (i.e., wherein the base of one face is on one side of the plane that defines the perimeter of the blaine and the base of the other face is on the opposite side of the plane that defines the perimeter of the blaine), or between about minus one (−1) degree and about −2 degrees, or between about −2 degrees and about −5 degrees, or between about −5 degrees and about −10 degrees, or between about −10 degrees and about −15 degrees, or between about −15 degrees and about −20 degrees, or between about −20 degrees and about −25 degrees, or between about −25 degrees and about −30 degrees.

Figure 2A:
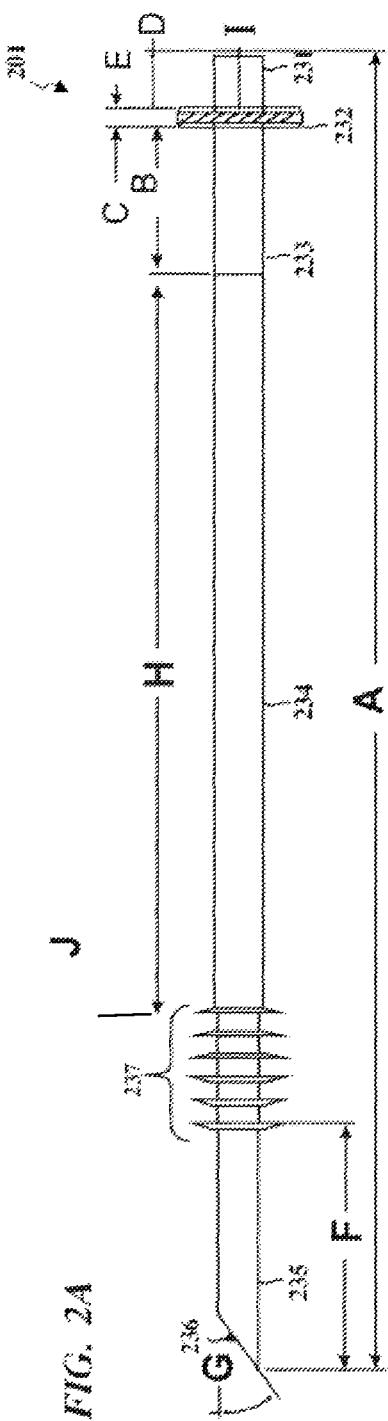
FIG. 2A is a schematic side-view of an endotracheal tube 201 having a Blaine Bafflex System, according to some embodiments of the present invention.

FIG. 2A is a schematic side view of an endotracheal tube 201 having a Blaine Bafflex System 237, according to some embodiments of the present invention. In some embodiments, Blaine Bafflex System 237 includes a plurality of blaines (e.g., six in the present figure), the shape and size of the blaines is selected according to the desired use of endotracheal tube 201. In FIG. 2A, dimension "A" refers to the entire length of endotracheal tube 201, dimension "B" refers to the length of thick-walled section 233 (i.e., the distance from the left side (with respect to the figure) of flange 232 to the left end of thick-walled section 233, the dimension bounded between "C" and "E" refers to the length of flange 232, the dimension "D" refers to the length of end piece 231, the dimension "F" refers to the length of tip section 235 (i.e., the distance between the left-most blaine of Blaine Bafflex System 237 (according to the figure) and the tip of tube 201), dimension "G" refers to the angle the end tip 236 makes with the central axis (i.e., axis-line "I") of tube 201, dimension "H" refers to the length of central section 234 (i.e., the distance between the left-most end of thick-walled section 233 and the right-most blaine of Blaine Bafflex System 237) In some embodiments, dimension "A" is selected according to the size of the patient (e.g., adult versus child or small animal versus large animal). In some embodiments, the diameter of end piece 231 and piece 232 is wider than the diameter of central section 234 and tip section 235. In some embodiments, tube 201 has an internal diameter that is substantially constant down the entire length of tube 201 and is selected according to the size of the patient. In some other embodiments, tube 201 has an internal diameter that is not substantially constant down the entire length of tube 201 and instead the internal diameter is selected for each portion of tube 201 (i.e., for end cap 231, flange 232, thick-walled section 233, central section 234, Blaine Bafflex System 237, tip piece 235, and end tip 236) according to the desired rigidity or flexibility of each respective section. In some embodiments, the end tip 236 of tube 201 is inserted first through the mouth of the patient and into the patient's trachea. In some embodiments, the length "F" of tip section 235 is designed to be long enough to allow the practitioner using inserting tube 201 into a patient to see the end tip 236 and a portion of tip section 235 beyond blaines 237 when the throat of the patient is curved, which, in some instances, negates the need for the use of a stylet as required when inserting a conventional intubation tube having an inflation cuff into a patient having a curved throat because the tip of the end portion of a conventional tube is not visible when inserting a conventional tube into a curved throat.

Some of the measurements described herein are denoted in inches, wherein 1 inch is equal to 2.54 cm. In some embodiments, dimension "A" is about 40 cm, dimension "B" is about 5 cm, the distance bounded by dimension "C" and dimension "E" is about 0.6 cm, dimension "D" is about 1.8 cm, dimension "F" is about 6.35 cm, angle "G" is about 45 degrees, and dimension "H" is about 19.05 cm. In some other embodiments, dimension "A" is between about 10 cm and about 25 cm, or between about 25 cm and about 50 cm, or between about 50 cm and about 75 cm, dimension "B" is between about 1 cm and about 1 inch, or between about 1 inch and about 1.5 inches, or between about 1.5 inches and about 2 inches, or between about 2 inches and about 2.5 inches, or between about 2.5 inches and about 3 inches, or between about 3 inches and about 4 inches, or between about 4 inches and about 15 cm; the distance bounded by dimension "C" and dimension "E" is between about 0.125 inches and about 0.25 inches, or between about 0.25 inches and about 0.5 inches, or between about 0.5 inches and about 0.75 inches, or between about 0.75 inches and about 1 inch, or between about 1 inch and about 1.5 inches, or between about 1.5 inches and about 2 inches; dimension "D" is between about 0.25 inches and about 0.5 inches, or between about 0.5 inches and about 1 inch, or between about 1 inch and about 1.5 inches, or between about 1.5 inch and about 2 inches, or between about 2 inches and about 2.5 inches, or between about 2.5 inches and about 3 inches, or between about 3 inches and about 4 inches, or between about 4 inches and about 5 inches; dimension "F" is between about 1 inch and about 2 inches, or between about 2 inches and about 3 inches, or between about 3 inches and about 4 inches, or between about 4 inches and about 5 inches, or between about 5 inches and about 7.5 inches, or between about 7.5 inches and about 10 inches; angle "G" is between about 20 degrees and about 25 degrees, or between about 25 degrees and about 30 degrees, or between about 30 degrees and about 35 degrees, or between about 35 degrees and about 40 degrees, or between about 40 degrees and about 45 degrees, or between about 45 degrees and about 50 degrees, or between about 50 degrees and about 55 degrees, or between about 55 degrees and about 60 degrees; and dimension "H" is between about 5 inches and about 6 inches, or between about 6 inches and about 7 inches, or between about 7 inches and about 8 inches, or between about 8 inches and about 9 inches, or between about 9 inches and about 10 inches.

Figure 2B:
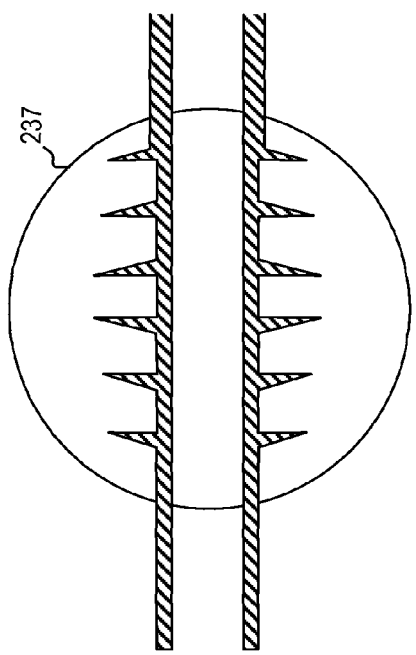
FIG. 2B is a schematic side-view cross-section of a portion of endotracheal tube 201 showing close-up view of the Blaine Bafflex System, according to some embodiments of the present invention.

FIG. 2B is a schematic side-view cross-section of a portion of endotracheal tube 201 showing a close-up view of the Blaine Bafflex System 237, according to some embodiments of the present invention. In some embodiments, as discussed above, Blaine Bafflex System 237 includes a plurality of six blaines integrated with tube 201. In some embodiments, the left-most three blaines (with respect to the figure) have blaines that are tapered and are substantially flat on the right side of each blaine and are angled with respect to a plane that is perpendicular to the axis of tube 102 on the left side of each blaine and the right-most three blaines (with respect to the figure) have blaines that are tapered and are substantially flat on the left side of each blaine and are angled with respect to a plane that is perpendicular to the axis of tube 102 on the right side of each blaine. In some embodiments, the circumference of the blaines increases towards the center of Blaine Bafflex System 237 (i.e., the two outer-most blains have the smallest circumference and the two inner-most blaines have the largest circumference.

Figure 3:
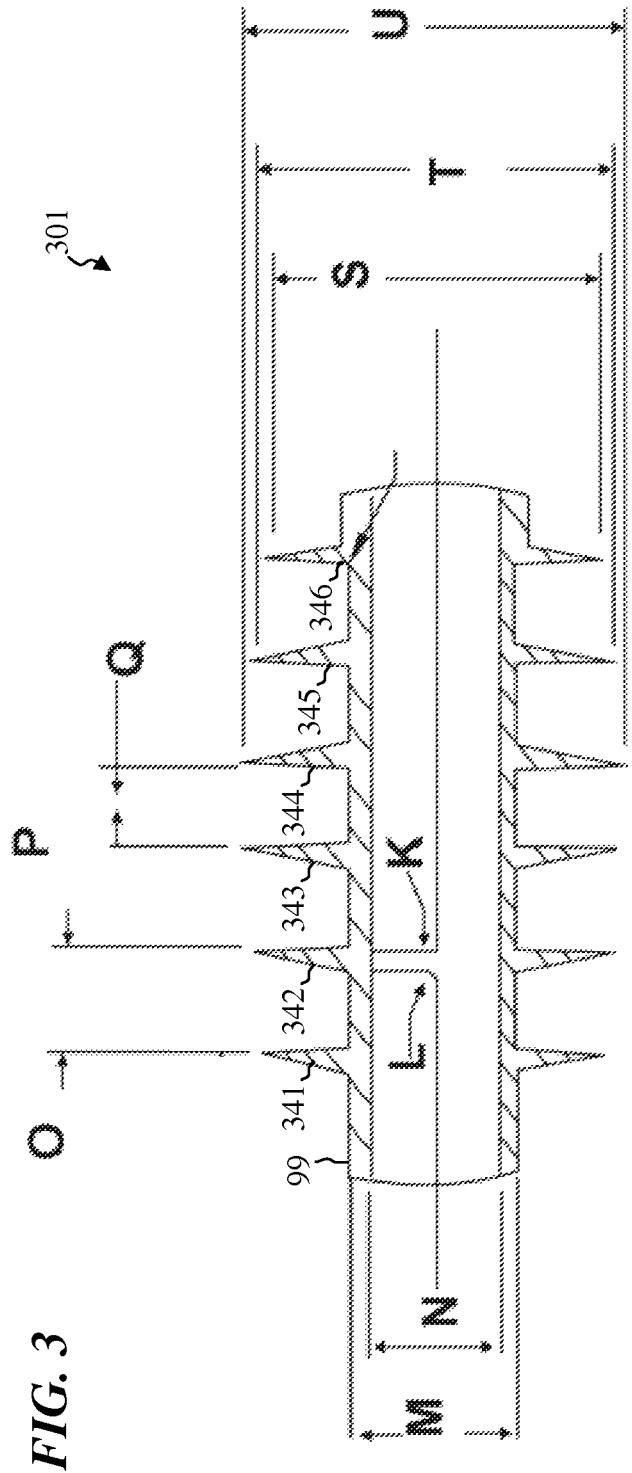
FIG. 3 is a schematic side-view cross-section of a Blaine Bafflex System 301, according to some embodiments of the present invention.

FIG. 3 is a schematic side-view cross-section of a Blaine Bafflex System 301, according to some embodiments of the present invention. In FIG. 3, the angle bounded between "L" and "K" refers to the angle created between a plane perpendicular to the axis of tube 99 and the sloped side of blaine 342, dimension "M" refers to the outer diameter of tube 99, dimension "N" refers to the inner diameter of tube 99, the dimension bounded between "O" and "P" refers to the distance between the flat side of blaine 341 and the flat side of blaine 342, dimension "Q" refers to the distance between blaine 343 and blaine 344, dimension "S" refers to the maximum diameter of blaine 346, dimension "T" refers to the maximum diameter of blaine 345, and dimension "U" refers to the maximum diameter of blaine 344. In some embodiments, blaine 341 and blaine 346 have substantially the same outer circumference, blaine 342 and blaine 345 have substantially the same outer circumference, and blaine 343 and blaine 344 have substantially the same outer circumference.

In some embodiments, the angle bounded between "K" and "L" is about 8 degrees, dimension "M" is about 0.42 inches, dimension "N" is about 0.3 inches, the length bounded between "O" and "P" is about 0.325 inches, the dimension "Q" is about 0.25 inches, the dimension "S" is about 0.682 inches, the dimension "T" is about 0.758 inches, and the dimension "U" is about 0.837 inches. In some other embodiments, the angle bounded between "K" and "L" is between about 5 degrees and 6 degrees, or between about 6 degrees and 7 degrees, or between about 7 degrees and 8 degrees, or between about 8 degrees and 9 degrees, or between about 9 degrees and 10 degrees, or between about 10 degrees and 12 degrees, or between about 12 degrees and 15 degrees; dimension "M" is between about 0.3 inches to about 0.35 inches, or between about 0.35 inches to about 0.4 inches, or between about 0.4 inches to about 0.45 inches, or between about 0.45 inches to about 0.5 inches, or between about 0.5 inches to about 0.55 inches, or between about 0.55 inches to about 0.6 inches, or between about 0.6 inches to about 0.65 inches, or between about 0.65 inches to about 0.7 inches, or between about 0.7 inches to about 0.75 inches; dimension "N" is between about 0.1 inches to about 0.15 inches, or between about 0.15 inches to about 0.2 inches, or between about 0.2 inches to about 0.25 inches, or between about 0.25 inches to about 0.3 inches, or between about 0.3 inches to about 0.35 inches, or between about 0.35 inches to about 0.4 inches, or between about 0.4 inches to about 0.45 inches, or between about 0.45 inches to about 0.5 inches, or between about 0.5 inches to about 0.55 inches; the length bounded between "O" and "P" is between about 0.1 inches to about 0.15 inches, or between about 0.15 inches to about 0.2 inches, or between about 0.2 inches to about 0.25 inches, or between about 0.25 inches to about 0.3 inches, or between about 0.3 inches to about 0.35 inches, or between about 0.35 inches to about 0.4 inches, or between about 0.4 inches to about 0.45 inches, or between about 0.45 inches to about 0.5 inches; the dimension "Q" is between about 0.05 inches to about 0.1 inches, or between about 0.1 inches to about 0.15 inches, or between about 0.15 inches to about 0.2 inches, or between about 0.2 inches to about 0.25 inches, or between about 0.25 inches to about 0.3 inches, or between about 0.3 inches to about 0.35 inches, or between about 0.35 inches to about 0.4 inches, or between about 0.4 inches to about 0.45 inches, or between about 0.45 inches to about 0.5 inches, or between about 0.5 inches to about 0.55 inches; the dimensions "S", "T", and "U" are between about 0.1 inches to about 0.15 inches, or between about 0.15 inches to about 0.2 inches, or between about 0.2 inches to about 0.25 inches, or between about 0.25 inches to about 0.3 inches, or between about 0.3 inches to about 0.35 inches, or between about 0.35 inches to about 0.4 inches, or between about 0.4 inches to about 0.45 inches, or between about 0.45 inches to about 0.5 inches, or between about 0.5 inches to about 0.55, or between about 0.55 inches to about 0.6 inches, or between about 0.6 inches to about 0.65 inches, or between about 0.65 inches to about 0.7 inches, or between about 0.7 inches to about 0.75 inches, or between about 0.75 inches to about 0.8 inches, or between about 0.8 inches to about 0.85 inches, or between about 0.85 inches to about 0.9 inches, or between about 0.9 inches to about 0.95 inches, or between about 0.95 inches to about 1 inch, or between about 1 inch to about 1.15 inches, or between about 1.15 inches to about 1.3 inches, or between about 1.3 inches to about 1.5 inches.

Figure 4:
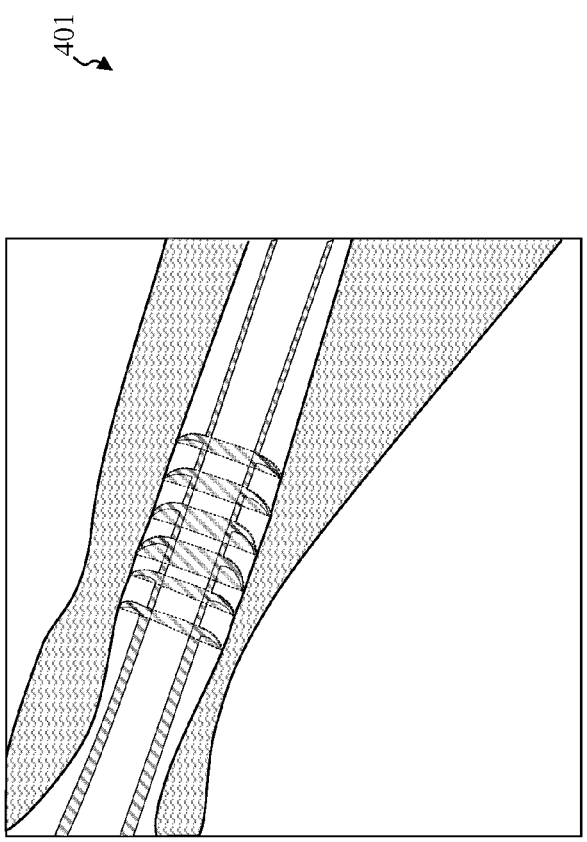
FIG. 4 is an X-ray image of an endotracheal tube 401 having a Blaine Bafflex System inserted into the trachea of a patient (i.e., a dog), according to some embodiments of the present invention.

FIG. 4 is an X-ray image of an endotracheal tube 401 having a Blaine Bafflex System 437 inserted into the trachea of a patient (i.e., a dog), according to some embodiments of the present invention. In some embodiments, the blaines of Blaine Bafflex System 437 of endotracheal tube 401 create an air and fluid seal between the inner surface of the trachea and the Blaine Bafflex System 437.

Figure 5:
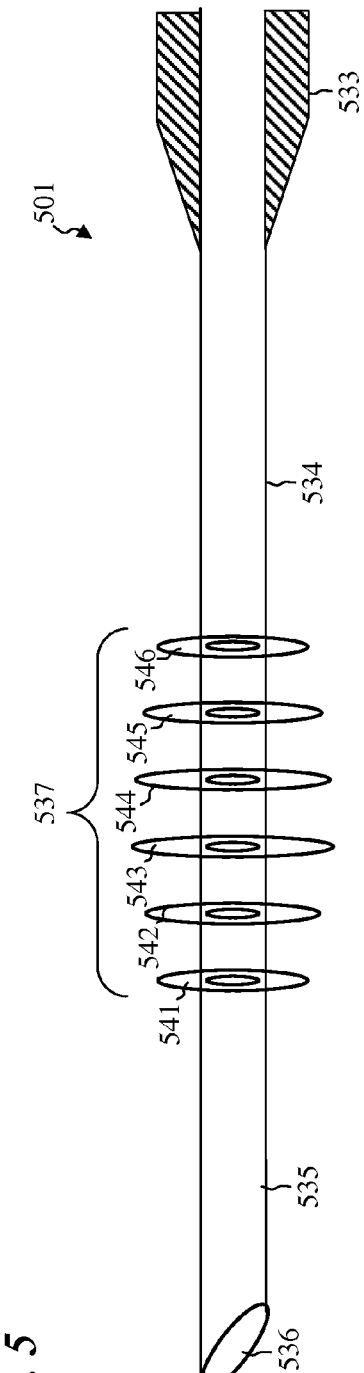
FIG. 5 is a schematic perspective view of a smaller endotracheal tube 501 having a Blaine Bafflex System with blaines having larger and smaller outer circumferences, designed for pediatric use or with small animals, according to some embodiments of the present invention.

FIG. 5 is a schematic perspective view of a smaller endotracheal tube 501 having a Blaine Bafflex System 537 with blaines (541, 542, 543, 544, 545, and 546) having larger and smaller outer circumferences, designed for pediatric use or with small animals having smaller tracheas, according to some embodiments of the present invention. In some embodiments, endotracheal tube 501 includes thick-walled section 533, central section 534, end section 535, angled tip end 536, and Blaine Bafflex System 537. In some embodiments, blaines 541 and 546 have substantially the same outer circumference, blaines 542 and 545 have substantially the same outer circumference, and blaines 543 and 544 have substantially the same outer circumference.

Figure 6:
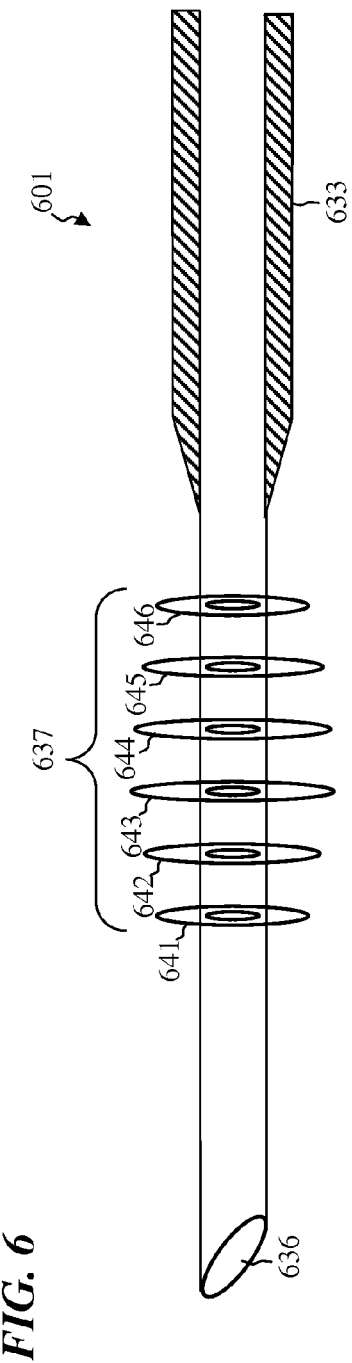
FIG. 6 is a schematic perspective view of a smaller endotracheal tube 601 having a Blaine Bafflex System with blaines having larger and smaller outer circumferences and a shorter distance between the blaines and the mouth end of the tube, designed for pediatric use or with small animals, according to some embodiments of the present invention.

FIG. 6 is a schematic perspective view of a smaller endotracheal tube 601 having a Blaine Bafflex System 637 with blaines (641, 642, 643, 644, 645, and 646) having larger and smaller outer circumferences and a shorter distance between the Blaine Bafflex System 637 and the thick-walled section 633, designed for pediatric use or with small animals, according to some embodiments of the present invention. In some embodiments, endotracheal tube 601 is substantially similar to endotracheal tube 501 discussed above, except that the central section 634 is substantially shorter than central section 534 and therefore thick-walled section 633 is substantially longer than thick-walled section 533 and the end of thick-walled section 633 is substantially closer to the Blaine Bafflex System 637.

Figure 7:
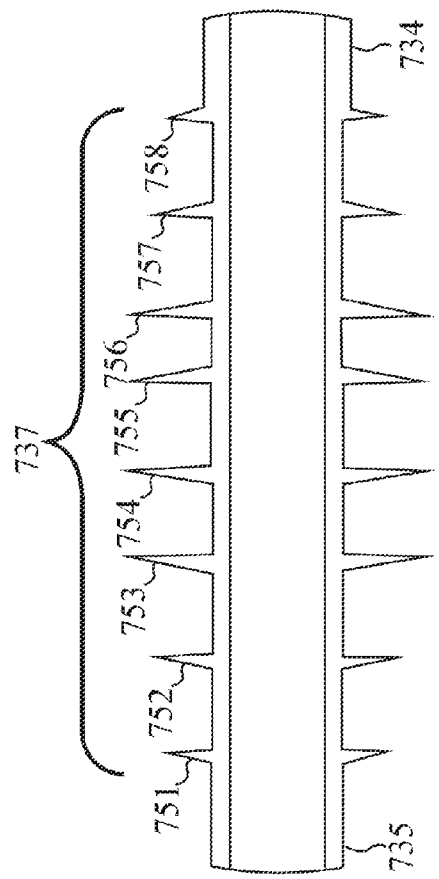
FIG. 7 is a schematic side-view cross-section of an endotracheal tube portion 701, wherein the outer circumference of each of the plurality of blaines is selected to provide a desired function, according to some embodiments of the present invention.

FIG. 7 is a schematic side-view cross-section of an endotracheal tube portion 701, wherein the outer circumference of each of the plurality of blaines (751, 752, 753, 754, 755, 756, 757, and 758) is selected to provide a desired function, according to some embodiments of the present invention. In some embodiments, Blaine Bafflex System 737 is located between the end section 735 and central section 734 (only a portion of end section 735 and central section 734 are shown in FIG. 7), and includes blaines 751, 752, 753, 754, 755, 756, 757, and 758. In some embodiments, blaines 751, 752, 753, and 754 are tapered with the right side of each blaine being substantially flat (i.e., perpendicular to the axis of tube portion 701) and the left side of each blaine creating an angle with a plane formed perpendicular to the axis of tube portion 701. In some embodiments, blaines 755, 756, 757, and 758 are tapered with the left side of each blaine being substantially flat (i.e., perpendicular to the axis of tube portion 701) and the right side of each blaine creating an angle with a plane formed perpendicular to the axis of tube portion 701. In some embodiments, blaines 751 and 758 have substantially the same outer circumference, blaines 752 and 757 have substantially the same outer circumference, and blaines 753, 754, 755, and 756 have substantially the same outer circumference.

FIG. 8 is a schematic side-view cross-section of an endotracheal tube portion 801, wherein the outer circumference of each of the plurality of blaines is selected to provide a desired function, according to some embodiments of the present invention. In some embodiments, Blaine Bafflex System 837 is located between the end section 835 and central section 834 (only a portion of end section 835 and central section 834 are shown in FIG. 8), and includes blaines 861, 862, 863, 864, 865, 866, 867, and 868. In some embodiments, blaines 861, 862, 863, and 864 are tapered with the right side of each blaine being substantially flat (i.e., perpendicular to the axis of tube portion 801 and the left side of each blaine creating an angle with a plane formed perpendicular to the axis of tube portion 801. In some embodiments, blaines 865, 866, 867, and 868 are tapered with the left side of each blaine being substantially flat (i.e., perpendicular to the axis of tube portion 801 and the right side of each blaine creating an angle with a plane formed perpendicular to the axis of tube portion 801. In some embodiments, blaines 861 and 868 have substantially the same outer circumference, blaines 862 and 867 have substantially the same outer circumference, blaines 863 and 866 have substantially the same outer circumference, and blaines 864 and 865 have substantially the same outer circumference. In some embodiments, the outer-most blaines (861 and 868) of Blaine Bafflex System 837 have the smallest outer circumference and the size of the outer circumference increases with each next inner pair of blaines.

FIG. 9 is a schematic side-view cross-section of an endotracheal tube portion 901 having a Blaine Bafflex System 937, wherein Blaine Bafflex System 937 includes a plurality of blaines, according to some embodiments of the present invention.

Figure 10:
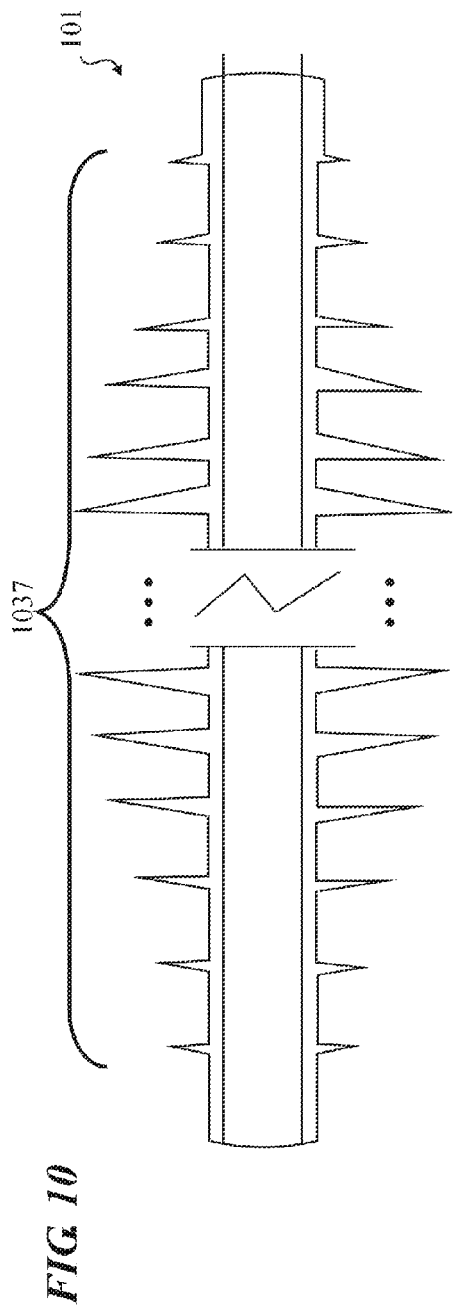
FIG. 10 is a schematic side-view cross-section of an endotracheal tube portion 1001 having two sets of blaines, wherein each set includes a plurality of blaines and wherein the two sets of blaines are separated a lateral distance, according to some embodiments of the present invention.

FIG. 10 is a schematic side-view cross-section of an endotracheal tube portion 1001 having a Blaine Bafflex System 1037, wherein Blaine Bafflex System 1037 includes a plurality of blaines and wherein the two sets of blaines are separated a lateral distance, according to some embodiments of the present invention.

Figure 11:
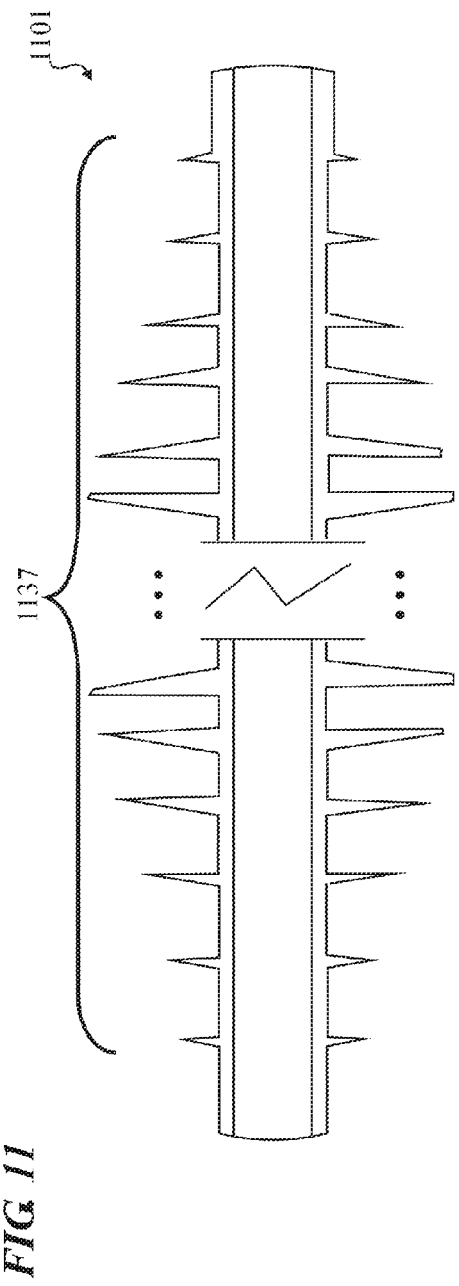
FIG. 11 is a schematic side-view cross-section of an endotracheal tube portion 1101 having two sets of blaines, wherein each set includes a plurality of blaines and wherein the two sets of blaines are separated a lateral distance, according to some embodiments of the present invention.

FIG. 11 is a schematic side-view cross-section of an endotracheal tube portion 1101 having a Blaine Bafflex System 1137, wherein Blaine Bafflex System 1137 includes a plurality of blaines and wherein the two sets of blaines are separated a lateral distance, according to some embodiments of the present invention.

In some embodiments, tube portion 901 is substantially similar to tube portion 701, tube portion 1001 is substantially similar to tube portion 801, except that tube portion 901 and tube portion 1001 have additional blaines. In some embodiments, tube portion 901 and tube 1001 have between about 5 and 10 blaines, or between about 10 and 15 blaines, or between about 15 and 20 blaines, or between about 20 and 25 blaines, or between about 25 and 30 blaines, or between about 30 and 35 blaines, or between about 35 and 40 blaines. In some embodiments, tube portion 1101 is substantially similar to tube portion 1001 except that the blaines of tube portion 1101 are arranged in a manner such that some of the blaines are "flipped" (i.e., the "angled side" and the "flat side" are on opposite sides as the corresponding blaines in tube portion 1001).

Figure 12:
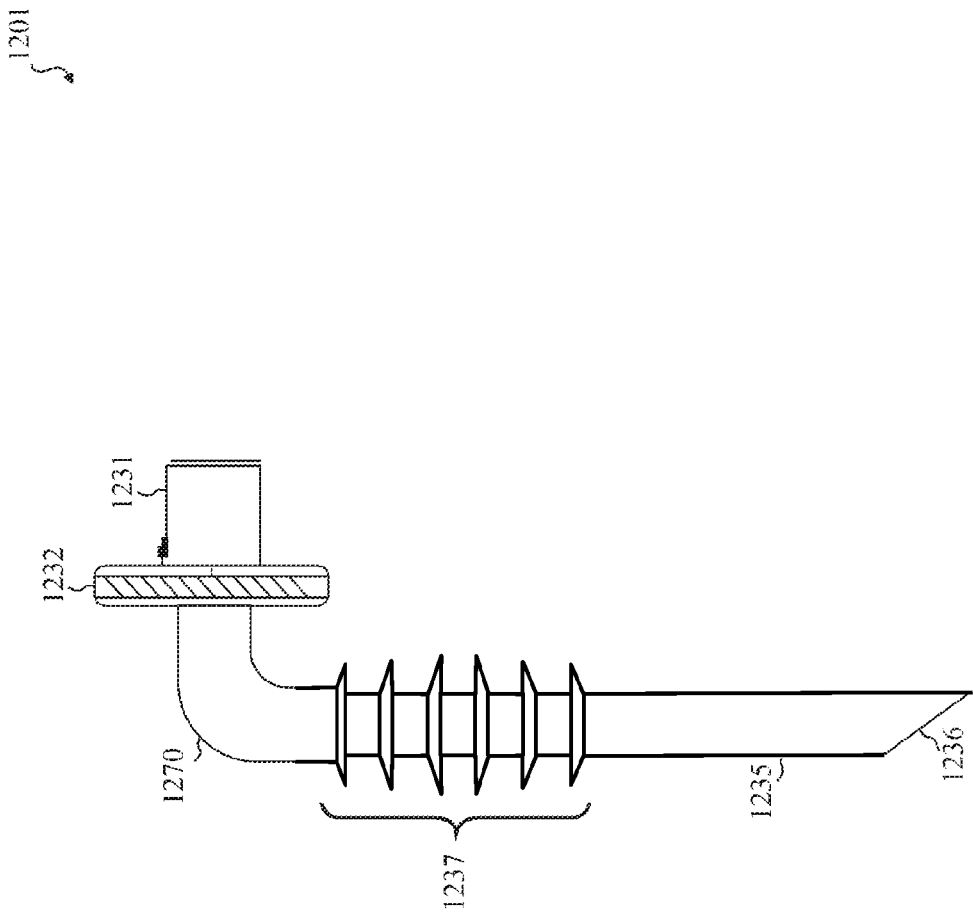
FIG. 12 is a schematic side view of an angled endotracheal tube 1201 having a Blaine Bafflex System, according to some embodiments of the present invention.

FIG. 12 is a schematic side view of an angled endotracheal tube 1201 having a Blaine Bafflex System, according to some embodiments of the present invention. In some embodiments, angled endotracheal tube 1201 includes end piece 1231, flange 1232, angled portion 1270, Blaine Bafflex System 1237, end section 1235, and angled end tip 1236. In some embodiments, angled endotracheal tube 1201 is used for patients and animals that have a curved throat to assist with tube insertion.

In some embodiments, the present invention provides an intubation tube that is constructed in one continuous piece to help avoid contamination. In some embodiments, this tube is made of 100% medical grade silicone to enable the tube to be sterilized in an autoclave.

In some embodiments, the apparatus is straight without curves or bends. In other embodiments the invention is curved and has a bend.

In some embodiments of the invention, the tube is made with thinner wall thickness which makes the tube more flexible. In other embodiments of the invention, the tube is made with thicker walls which make the tube more ridged and robust.

In some embodiments of the invention, the tip of tube is not touching trachea due to lack of a rigid curve.

In some embodiments of the invention a stylet is used.

In some embodiments of the invention the tip is angled, not blunt, enabling easier insertion through the glottis In some embodiments of the invention, the blaines, or the Blaine Bafflex System, are spaced further from tip allowing visualization of the tip of the tube when inserting in the throat (see dimension F in FIG. 2A).

In some embodiments of the invention, the blaines are substantially perpendicular to the tube on one side and tapered the other side.

In some embodiments of the invention, the blaines have diameters of different sizes, and in other embodiments there are six or more blaines that have 3 different outer circumferences.

In some embodiments of the invention the first three blaines have the angled side facing proximally and correspondingly, the last blaines have the angle facing caudally, allowing the tube to seal when moved in either direction.

In some embodiments of the invention the blaines are optimally spaced apart to achieve the best seal. When the tube is inserted in the trachea, the blaines bend to create the seal. In some embodiments, when the blaines bend they require enough space between the blains so the blains do not touch one another.

In some embodiments of the invention the proximal portion of our tube is thicker to make the tube easier to insert and withdraw from the patient and to protect the patient.

In some embodiments of the invention the uniquely flexible shaft, in some embodiments made of silicone, allows patient rotation so tip does not cause damage. In other instances, the patient can be rotated with the tube inserted in the trachea, where traditional conventional inflation cuff tubes with balloons need to be deflated if the patient is to be moved or there is a risk of damaging the trachea, vocal cords and other tissue. In some embodiments of the invention the patient can be rotated without disconnecting from machine.

In some embodiments of the invention there is a corresponding Stylet, which can be made with different materials, PVC, vinyl coated wire, aluminum, copper, etc. (commercially available stylets are often copper because it is malleable thereby allowing the tube to be made to curve, especially for human use.)

In some embodiments, the intubation tube includes a stylet that has a finger grip.

In some embodiments, the intubation tube includes a semi-rigid stylet, formed curve stylet, and a formable stylet.

In some embodiments of the invention, the blaines have a specific thickness at the base of the Blaine that is specific to the size and diameter of the Blaine to optimize the effectiveness of the seal that the Blaine provides.

In some embodiments of the invention, the taper of the blaines are specific for each corresponding size tube.

In some embodiments of the invention, the wall thickness is specifically optimized for each size tube. In one such embodiment, a middle size tube has larger diameter shaft than the tip. In another embodiment, a smaller tube has larger diameter shaft than the tip. In yet another embodiment, a smaller tube has a "cone" from a wider shaft down to first Blaine.

In some embodiments of the invention the Blaine Bafflex System includes between 1 and 24 blaines.

In some embodiments of the invention the Blaine Bafflex System includes between 3 and 24 blaines.

In some embodiments of the invention the blaines are manufactured in conjunction with the rest of the tube and the adapter at the end of the tube, all within one mold.

In some embodiments of the invention the apparatus contains a taper of an adapter to fit a y-tube of a standard anesthetic machine. In some embodiments this allows for a snug fit because the plastic inner diameter (I.D.) of the y-tubes varies and often allow a rigid adaptor to slip loose. In some embodiments of the invention the silicone is tapered and the adaptor on the apparatus adjusts for variances.

In some embodiments of the invention there is an added apparatus, or stylet that is used to insert the device. In some embodiments, the stylet apparatus is ridged and in other embodiments, the apparatus is formable, or bendable to a specific shape.

In some embodiments of the invention it is easier for the user to select the correct size of tube to use because the invention fits a larger number of sizes of tracheas. This translates in some embodiments to less inventory and less training, when compared to traditional inflation cuffs, to meet the various sizes of tracheas.

In some embodiments of the invention a laryngeal scope is not necessary due to distance between tip and Baffles system. This allows the user who is inserting the tube in the trachea to see the location of the tip to direct the tip in to the trachea.

In some embodiments of the invention, one method is using a smaller version of the invention which is inserted until the cone contacts the glottis to insure that the flexible tip is inside the glottis/larynx.

In some embodiments of the invention the method is easier then placing traditional, more ridged tubes, because the invention does not have a pre-formed curve in the tube, therefore, it does not matter how the invention is positioned in the mouth or where it exits.

In some embodiments of the invention, the device is reusable and more aseptic due to one piece construction and easier, more efficient cleaning.

In some embodiments of the invention the Bafflex system can be used in other methods and applications which are non-medical. In embodiments where a smaller tube needs to be sealed inside a larger tube such as putting a small ¼ inch tube in a garden hose to water plants, or in my case, or inserting a smaller tube in the larger oil change tube to suck the oil out of a boat engine through the dip stick hole.

In some embodiments of the invention the insertion method utilizes an angled tip of the tube to pry the arytenoids cartilages apart for insertion.

In some embodiments of the invention, the devices use a blunt surface.

In some embodiments of the invention, the method used to insert the device prevents blocked or occluded tips. In one such embodiment, the tip of the tube is always centered in the trachea, as opposed to traditional tubes with curves, so the operator does not have to worry about the tip of the tube being occluded because the tip is resting against the tracheal wall. Traditional conventional curved tubes require a hole in the side of the tube near the tip, commonly called a Murphy Eye to prevent the situation in which the normal opening at the tip is occluded because it is up against the tracheal wall. The method the invention provides is easier for the operator or user of the tube who is inserting the invention in to the trachea. The new method using the apparatus, is safer, saves time and is easier for the user because the operator does not have to perform a critical safety test to observe and test the ventilation of the patient after intubation to insure the tip of the tube is not occluded.

Traditional means of removing traditional tubes, or extubating a pre-formed, curved, rigid tube, it is important that it is extracted with an arch or curving hand motion in the shape of the tube to prevent the tip from scraping the tracheal wall and vocal cords. The new method with the invention provides for a means to easily remove the tube with a straight or any type of hand motion because the risk of damaging tissue is mitigated.

In some embodiments of the invention the method of extubating provides for a means to clean the trachea upon removable of the apparatus. The blaines provide for a gentle and evenly pressured mechanism to remove mucus from the trachea wall upon removal.

In some embodiments, the present invention provides a method that includes intubating a patient with a one-piece apparatus that is sized and placed in the patient's throat, and then connecting the apparatus to insufflation equipment. A minimally trained technician can use this tube because they don't need to be trained in the proper inflation of a cuff. In some embodiments, the tube must be stopped (brought to a halt) while inserting in a forward direction, in order that the tips of the distended blaines are pointing outward (towards the external orifice of the body passage into which the device has been inserted) in order to easily release excess gas pressure (e.g., if too much gas is inserted into the lungs, the blaines when distended in this direction will easily pass the gas outwards). In some embodiments, the flexibility or durometer of the plastic used for the blaines is selected to seal to a predetermined pressure but to then release gas if that pressure is exceeded. There is no inflation required with this method. The tube is withdrawn 1 to 2 cm if the operator desires positive ventilation pressure above 20-30 centimeters of water.

Selecting the proper size of tube is easier because only 3 sizes are necessary for patients ranging from 10 to 200 pounds. The smallest tube is inserted until the flare on the tube is in contact with the glottis. A stylet is used to insert the tube which allows a softer, atraumatic and a safer tube to be used. When first inserted the operator will ignore sounds of leakage of the tube during forceful expirations as this is normal with this method. Upon reaching the proper level of anesthetic if any leakage is detected the tube is exchanged for a tube of the larger size.

When using inflation cuff tubes it is imperative that the operator check the pop-off valve for patentcy. It is not critical that the pop-off valve be open when using the Bafflex System with the blaines. After inserting the tube the patient can be rotated without disconnecting from the anesthetic machine as opposed to inflation cuff tubes in which it is critical that the patient be disconnected before rotation. The new method means that technicians don't need as much training, since there is no inflatable cuff.

Some embodiments further include implementing the method with an apparatus that has blaines that seal the trachea which mitigate damage to the trachea by limiting the maximum pressure that can be exerted to the wall of the trachea down to 1-3 centimeters of water pressure as opposed to 20-40 centimeters of inflation cuff tubes; has blaines that mitigate damage to the trachea if left for extended periods of time due to the absence of pressure points; has blaines specifically designed to enable the patient to be rotated during surgery without risk of damage to the trachea; has blaines designed to remove all fluids from the trachea upon extubation; has an adapter designed to enable easier and more effective attachment of the Y tube connector of the insufflation equipment; has an adapter designed to enable easier and more effective removal of the Y tube connector of the insufflation equipment; has a more user friendly finger grip for removal of the tube; has a larger, flared finger grip which prevents the tube from being inserted too deeply; and/or is constructed as a one-piece mitigating and eliminating the failure of multiple parts. In some embodiments, its one-piece construction eliminates the need for assembly of different materials and mitigates contamination potential. In some embodiments, it is composed of 100% medical-grade silicone allowing sterilization by autoclave, a commonly used technique in most hospitals. Its single piece construction is much more durable and with proper care will remain usable for many years. In some embodiments, it is manufactured to be transparent to enable the physician to see fluids in the tube. In some embodiments, the tube is designed to accommodate a much larger range of sizes of tracheas making it only necessary to stock just a few (e.g., in some embodiments, only three) sizes of tube versus up to fourteen sizes needed with traditional inflation-cuff tubes.

Some embodiments further include reversing the blaines in the trachea by inserting the tube a little further than the final desired position and then pulling on the tube to reverse the direction of the blaines (such that the tip circumferences point inward) to enable larger pressure to be applied in the lungs than if the tip circumferences point outward (as is the case of the tube is left in the position of furthest insertion.

Some embodiments further include using the tube and blaines to clean the trachea by inserting and withdrawing the tube one or more times.

In some embodiments, the present invention provides an intubation device that includes a flexible lumen (i.e., a tube having a diameter that is smaller than that of a normal tracheal passage) having a distal end for insertion into the tracheal passage and a proximal end having a plurality of spaced-apart flexible resilient annular blaines located at a distance from a distal end and at a distance from a proximal end, and formed integral on the lumen as a single piece, wherein the distal end is configured to be inserted into a body passage and the proximal end is configured to be outside the body and attached to a medical device such as a respirator.

In some embodiments, the flexible resilient annular blaines have the shape of an extended parasol if no force is applied, but are designed to distend and conform to an inner surface of a body passage (e.g., the tracheal passage of an animal patient such as a dog, cat, or human) when inserted into such a passage in order to releasably seal the passage. When the intubation device is inserted to its maximal extent within the passageway, each one of a plurality of the blaines is distended such that their outer circumference is bent toward the central axis of the lumen in a direction toward the proximal end of the lumen (i.e., the outer circumference is closer to the proximal end than is the base of the blaine adjacent the lumen.

When in this first fully inserted position, the seal against the trachea can be overcome by an increase in pressure in the lungs (such as from an undesired excess of gas inserted into the lungs through the lumen from an external breathing machine, or a cough), because the excess pressure pushes the circumference of the blaine away from the tracheal wall. If the intubation device is then slightly withdrawn (e.g., 1-2 centimeters from its maximal extent), a plurality of the blaines will flip such that they are distended such that their outer circumference is bent toward the central axis of the lumen but in a direction toward the distal end of the lumen. When in this second partially withdrawn position, it takes a much higher pressure to overcome the seal against the trachea, because the excess pressure pushes the circumference of the blaine towards the tracheal wall.

In some embodiments, the present invention provides an apparatus that includes an intubation device having a flexible lumen having a proximal end and a distal end and a plurality of spaced-apart flexible resilient annular blaines located between the distal end the proximal end and formed integral on the lumen as a single piece, wherein the distal end is configured to be inserted into a body passage and the proximal end is configured to be outside the body and attached to a medical device.

In some embodiments of the apparatus, a plurality of the blaines formed on the lumen of the intubation device closest to the distal end have a smaller circumference than other blaines that are further from the distal end.

In some embodiments, a plurality of the blaines formed on the lumen of the intubation device closest to the proximal end have a smaller circumference than other blaines that are further from the proximal end.

In some embodiments, a one of the plurality of the blaines formed on the lumen of the intubation device that is second closest to the proximal end has a larger circumference than a one of the plurality of the blaines that is closest to the proximal end and a smaller circumference than a one of the plurality of the blaines that is third closest to the proximal end, and wherein a one of the plurality of the blaines formed on the lumen of the intubation device that is second closest to the distal end has a larger circumference than a one of the plurality of the blaines that is closest to the distal end and a smaller circumference than a one of the plurality of the blaines that is third closest to the distal end.

In some embodiments, the plurality of blaines includes a plurality of larger-circumference blaines located between those blaines that are closest, second closest, and third closest to the proximal end and those blaines that are closest, second closest, and third closest to the distal end.

In some embodiments, a plurality of the plurality of the blaines formed on the lumen of the intubation device closest to the proximal end each have a first face facing and closer to the proximal end having a substantially conical shape and a second face closer to the distal end having a substantially planar shape, and a plurality of the plurality of the blaines formed on the lumen of the intubation device closest to the distal end each have a first face facing and closer to the distal end having a substantially conical shape and a second face closer to the proximal end having a substantially planar shape.

In some embodiments, the plurality of the blaines integrally formed on the lumen of the intubation device include N blaines, including a first blaine closest to the proximal end having a first face facing and closer to the proximal end having a substantially conical shape and a second face facing and closer to the distal end having a substantially planar shape, a second blaine second closest to the proximal end having a first face facing and closer to the proximal end having a substantially conical shape and a second face facing and closer to the distal end having a substantially planar shape, wherein the second blaine has a larger circumference than that of the first blaine, an $N^{th}$ blaine closest to the distal end having a first face facing and closer to the distal end having a substantially conical shape and a second face facing and closer to the proximal end having a substantially planar shape, an $N-1^{st}$ blaine second closest to the distal end having a first face facing and closer to the distal end having a substantially conical shape and a second face facing and closer to the proximal end having a substantially planar shape, wherein the second blaine has a larger circumference than that of the first blaine, and a plurality of additional blaines formed on the lumen of the intubation device between the second blaine and the $N-1^{st}$ blaine each have a first face having a substantially conical shape and a second face having a substantially planar shape.

In some embodiments, the intubation device in its entirety is made of material that is autoclaveable with substantially no damage. In some embodiments, the intubation device in its entirety is made of a single material that is autoclaveable with substantially no damage.

In some embodiments, the present invention provides a method that includes providing an intubation device that includes a flexible lumen having a proximal end and a distal end and a plurality of spaced-apart flexible resilient annular blaines located between the distal end the proximal end, and formed integral on the lumen as a single piece; and sterilizing the intubation device as a single piece in its entirety.

In some embodiments of the method, the providing of the intubation device includes forming a plurality of the blaines on the lumen of the intubation device closest to the distal end to have a smaller circumference than other blaines that are further from the distal end.

In some embodiments of the method, the providing of the intubation device includes forming a plurality of the blaines on the lumen of the intubation device closest to the proximal end to have a smaller circumference than other blaines that are further from the proximal end.

In some embodiments of the method, the providing of the intubation device includes forming a one of the plurality of the blaines on the lumen of the intubation device that is second closest to the proximal end to have a larger circumference than a one of the plurality of the blaines that is closest to the proximal end and a smaller circumference than a one of the plurality of the blaines that is third closest to the proximal end, and forming a one of the plurality of the blaines formed on the lumen of the intubation device that is second closest to the distal end to have a larger circumference than a one of the plurality of the blaines that is closest to the distal end and a smaller circumference than a one of the plurality of the blaines that is third closest to the distal end.

In some embodiments of the method, the providing of the intubation device includes forming the plurality of blaines to include a plurality of larger-circumference blaines located between those blaines that are closest, second closest, and third closest to the proximal end and those blaines that are closest, second closest, and third closest to the distal end.

In some embodiments of the method, the providing of the intubation device includes forming a plurality of the plurality of the blaines on the lumen of the intubation device closest to the proximal end to each have a first face facing and closer to the proximal end having a substantially conical shape and a second face closer to the distal end having a substantially planar shape, and forming a plurality of the plurality of the blaines on the lumen of the intubation device closest to the distal end each have a first face facing and closer to the distal end having a substantially conical shape and a second face closer to the proximal end having a substantially planar shape.

In some embodiments of the method, the providing of the intubation device includes integrally forming the plurality of the blaines on the lumen to include N blaines, including a first blaine closest to the proximal end having a first face facing and closer to the proximal end having a substantially conical shape and a second face facing and closer to the distal end having a substantially planar shape, a second blaine second closest to the proximal end having a first face facing and closer to the proximal end having a substantially conical shape and a second face facing and closer to the distal end having a substantially planar shape, wherein the second blaine has a larger circumference than that of the first blaine, an $N^{th}$ blaine closest to the distal end having a first face facing and closer to the distal end having a substantially conical shape and a second face facing and closer to the proximal end having a substantially planar shape, an $N-1^{st}$ blaine second closest to the distal end having a first face facing and closer to the distal end having a substantially conical shape and a second face facing and closer to the proximal end having a substantially planar shape, wherein the second blaine has a larger circumference than that of the first blaine, and a plurality of additional blaines formed on the lumen between the second blaine and the $N-1^{st}$ blaine each have a first face having a substantially conical shape and a second face having a substantially planar shape.

In some embodiments of the method, the providing of the intubation device includes forming the plurality of blaines the intubation device in its entirety of a material that is autoclaveable with substantially no damage.

Some embodiments of the method further include inserting the distal end into a body passage, and attaching the proximal end outside the body to a medical device.

In some embodiments, the present invention provides an intubation device that includes a flexible lumen having a distal end for insertion into a body passage, and a proximal end; and a plurality of spaced-apart flexible resilient means (as described and shown herein) for sealing between the lumen and the body passage. In some embodiments of this apparatus, an outer circumference of each one of the plurality of flexible resilient means for sealing are substantially circular. In some embodiments of this apparatus, at least two of the plurality of flexible resilient means for sealing have a first face that is substantially conical and an opposite second face that is substantially planar. In some such embodiments, at least two of the plurality of flexible resilient means for sealing have a first face that is substantially conical facing the distal end of the lumen and an opposite second face that is substantially planar, while at least two others of the plurality of flexible resilient means for sealing have a first face that is substantially conical facing the proximal end of the lumen and an opposite second face that is substantially planar.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
   an intubation device that includes a flexible tube that surrounds a lumen that extends through the intubation device, wherein the tube has a proximal end and a distal end and a plurality of spaced-apart flexible resilient annular blaines located between the distal end and the proximal end, wherein the plurality of blaines and the tube are formed as a single monolithic piece of a single material that extends radially from the lumen of the tube to an outer circumference of each of the plurality of blaines, wherein each of the plurality of blaines is radially tapered from a first thickness at an inner radius to a second thickness at an outer radius, wherein the second thickness is thinner than the first thickness, and wherein the distal end is configured to be inserted into a body passage in a body of a patient and the proximal end is configured to be outside the patient's body and attached to a medical device.

2. The apparatus of claim 1, wherein a plurality of the plurality of blaines formed on the tube that surrounds the lumen of the intubation device closest to the distal end have a smaller circumference than another one of the plurality of blaines that is farther from the distal end.

3. The apparatus of claim 1, wherein a plurality of the plurality of blaines formed on the tube that surrounds the lumen of the intubation device closest to the proximal end have a smaller circumference than another one of the plurality of blaines that is farther from the proximal end.

4. The apparatus of claim 1, wherein one of the plurality of blaines formed on the tube that surrounds the lumen of the intubation device that is second closest to the proximal end has a larger circumference than another one of the plurality of blaines that is closest to the proximal end and a smaller circumference than yet another one of the plurality of blaines that is third closest to the proximal end, and wherein one of the plurality of blaines formed on the tube that surrounds the lumen of the intubation device that is second closest to the distal end has a larger circumference than
    another one of the plurality of blaines that is closest to the distal end and a smaller circumference than yet another one of the plurality of blaines that is third closest to the distal end.

5. The apparatus of claim 4, wherein the plurality of blaines includes a plurality of larger-circumference blaines located between those ones of the plurality of blaines that are closest, second closest, and third closest to the proximal end and those ones of the plurality of blaines that are closest, second closest, and third closest to the distal end.

6. The apparatus of claim 1, wherein
    a plurality of the plurality of blaines formed on the tube that surrounds the lumen of the intubation device closest to the proximal end each have a first face facing and closer to the proximal end having a substantially conical shape and a second face closer to the distal end having a substantially planar shape, and
    another plurality of the plurality of blaines formed on the tube that surrounds the lumen of the intubation device closest to the distal end each have a first face facing and closer to the distal end having a substantially conical shape and a second face closer to the proximal end having a substantially planar shape.

7. The apparatus of claim 1, wherein the plurality of blaines formed on the tube that surrounds the lumen of the intubation device include N blaines, wherein N is an integer, the N blaines including:
    a first blaine closest to the proximal end having a first face facing and closer to the proximal end having a substantially conical shape and a second face facing and closer to the distal end having a substantially planar shape,
    a second blaine second closest to the proximal end having a first face facing and closer to the proximal end having a substantially conical shape and a second face facing and closer to the distal end having a substantially planar shape, wherein the second blaine has a larger circumference than that of the first Blaine,
    an $N^{th}$ blaine closest to the distal end having a first face facing and closer to the distal end having a substantially conical shape and a second face facing and closer to the proximal end having a substantially planar shape,
    an $N-1^{st}$ blaine second closest to the distal end having a first face facing and closer to the distal end having a substantially conical shape and a second face facing and closer to the proximal end having a substantially planar shape, wherein the second blaine has a larger circumference than that of the first blaine, and
    a plurality of additional blaines formed on the tube that surrounds the lumen of the intubation device between the second blaine and the $N-1^{st}$ blaine each have a first face having a substantially conical shape and a second face having a substantially planar shape.

8. The apparatus of claim 1, wherein the intubation device in its entirety is made of material that is autoclaveable with substantially no damage.

9. The apparatus of claim 1, wherein the outer circumference of each one of the plurality of blaines is substantially circular.

10. The apparatus of claim 1, wherein at least two of the plurality of blaines have a first face that is substantially conical and an opposite second face that is substantially planar.

11. The apparatus of claim 1, wherein the distal end of the tube has a tip that is angled at a non-perpendicular angle to the lumen's axis, wherein the plurality of blaines are each tapered at an 11-degree angle from the first thickness at the inner radius of each respective one of the plurality of blaines to the second thickness at the outer circumference of the respective one of the plurality of blaines, and wherein the tube includes a tube wall that is thicker close to the proximal end than elsewhere along a length of the tube in order to prevent damage caused from biting on the tube by the patient, and wherein the tube and the plurality of blaines are one solid molded piece of silicone.

12. A method comprising:
    providing an intubation device that includes a flexible tube that surrounds a lumen that extends through the intubation device, wherein the tube has a proximal end and a distal end and a plurality of spaced-apart flexible resilient annular blaines located between the distal end and the proximal end, wherein the plurality of blaines and the tube are formed as a single monolithic piece of a single material that extends radially from the lumen to an outer circumference of each of the plurality of blaines, and wherein each of the plurality of blaines is radially tapered from a first thickness at an inner radius to a second thickness at an outer radius, wherein the second thickness is thinner than the first thickness;
    inserting the distal end into a body passage such that the plurality of blaines seals to walls of the body passage and the proximal end is outside the body passage; and
    attaching the proximal end to a medical device.

13. The method of claim 12, wherein
    a plurality of the plurality of blaines on the tube that surrounds the lumen of the intubation device closest to the distal end to have a smaller circumference than another one of the plurality of blaines that is farther from the distal end.

14. The method of claim 12, wherein
    a plurality of the plurality of blaines on the tube that surrounds the lumen of the intubation device closest to the proximal end to have a smaller circumference than another one of the plurality of blaines that is farther from the proximal end.

15. The method of claim 12, wherein
    one of the plurality of blaines on the tube that surrounds the lumen of the intubation device that is second closest to the proximal end to have a larger circumference than
    another one of the plurality of blaines that is closest to the proximal end and a smaller circumference than yet another one of the plurality of blaines that is third closest to the proximal end, and
    wherein one of the plurality of blaines formed on the tube that surrounds the lumen of the intubation device that is second closest to the distal end to have a larger circumference than another one of the plurality of blaines that is closest to the distal end and a smaller circumference than yet another one of the plurality of blaines that is third closest to the distal end.

16. The method of claim 15, wherein
the plurality of blaines includes a plurality of larger-circumference blaines located between those ones of the plurality of blaines that are closest, second closest, and third closest to the proximal end and those ones of the plurality of blaines that are closest, second closest, and third closest to the distal end.

17. The method of claim 12, wherein
a plurality of the plurality of blaines on the tube that surrounds the lumen of the intubation device closest to the proximal end to each have a first face facing and closer to the proximal end having a substantially conical shape and a second face closer to the distal end having a substantially planar shape, and
wherein another plurality of the plurality of blaines on the tube that surrounds the lumen of the intubation device closest to the distal end each have a first face facing and closer to the distal end having a substantially conical shape and a second face closer to the proximal end having a substantially planar shape.

18. The method of claim 12, wherein
the plurality of blaines on the tube that surrounds the lumen includes N blaines, wherein N is an integer, the N blaines including:
a first blaine closest to the proximal end having a first face facing and closer to the proximal end having a substantially conical shape and a second face facing and closer to the distal end having a substantially planar shape,
a second blaine second closest to the proximal end having a first face facing and closer to the proximal end having a substantially conical shape and a second face facing and closer to the distal end having a substantially planar shape, wherein the second blaine has a larger circumference than that of the first blaine,
an $N^{th}$ blaine closest to the distal end having a first face facing and closer to the distal end having a substantially conical shape and a second face facing and closer to the proximal end having a substantially planar shape,
an $N-1^{st}$ blaine second closest to the distal end having a first face facing and closer to the distal end having a substantially conical shape and a second face facing and closer to the proximal end having a substantially planar shape, wherein the second blaine has a larger circumference than that of the first blaine, and
a plurality of additional blaines formed on the tube that surrounds the lumen between the second blaine and the $N-1^{st}$ blaine each have a first face having a substantially conical shape and a second face having a substantially planar shape.

19. An apparatus comprising:
an intubation device that includes a flexible tube that surrounds a lumen, the intubation device having a distal end for insertion into a body passage, and a proximal end configured to be outside the body and attached to a medical device; and
a plurality of spaced-apart means for sealing between the tube that surrounds the lumen and the body passage, wherein the tube and the plurality of means for sealing are formed as a single monolithic piece of a single material.

20. The apparatus of claim 19, wherein an outer circumference of each one of the plurality of means for sealing are flexible, resilient, and substantially circular.

21. The apparatus of claim 20, wherein at least two of the plurality of means for sealing are flexible, resilient, and have a first face that is substantially conical and an opposite second face that is substantially planar, and wherein the first faces of the at least two of the plurality of means for sealing face in opposite directions.

\* \* \* \* \*